(12) United States Patent
Ford et al.

(10) Patent No.: US 6,780,612 B1
(45) Date of Patent: Aug. 24, 2004

(54) METHODS FOR THE PROPAGATION OF LYTIC ORGANISMS

(75) Inventors: Martin James Ford, Stevenage (GB); Paul Henry Hissey, Stevenage (GB); Tony James Pateman, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 31 days.

(21) Appl. No.: 10/018,700

(22) PCT Filed: Jun. 2, 2000

(86) PCT No.: PCT/EP00/05029

§ 371 (c)(1),
(2), (4) Date: Jun. 20, 2002

(87) PCT Pub. No.: WO01/02548

PCT Pub. Date: Jan. 11, 2001

(30) Foreign Application Priority Data

Jul. 1, 1999 (GB) .............................................. 9915413

(51) Int. Cl.$^7$ .................... C12N 1/00; C12N 15/861; C12N 7/02; C12N 5/00; C12P 21/00
(52) U.S. Cl. ................ 435/69.1; 435/235.1; 435/320.1; 435/455; 435/456; 435/471; 435/483; 435/398; 435/289.1; 435/5; 435/6; 435/239; 435/243; 435/261; 435/259
(58) Field of Search ............................. 435/320.1, 235.1, 435/455, 456, 471, 483, 69.1, 398, 298.1, 5, 6, 239, 243, 261, 259, 326, 325, 366, 382, 383, 395, 289.1, 297.4; 604/6.09; 210/646

(56) References Cited

U.S. PATENT DOCUMENTS 6,342,384 B1 * 1/2002 Chung et al. ............. 435/235.1
6,383,795 B1 * 5/2002 Carrion et al. .............. 435/239

FOREIGN PATENT DOCUMENTS

EP 0317874 5/1989
WO WO 95/27040 10/1995

OTHER PUBLICATIONS

Blasey et al., "Repeated hybridoma batch culture with cell recycle", *Cytotechnolgy* 13:1 51–53 (1993).
Chang et al., "High density cell culture membrane–based call recycle", *Biotechnology Advances* 12:3 467–487 (1994).
Radford et al., "Enhanced productivity in insect cell culture by control of the chemical environment", Chemical Abstracts Service, Access, No. 123:31369, *Anim. Cell Technol.: Basic Appl. Aspects. Proc. Int. Meet. Jpn. Assoc. Anim. Cell Technol.*, 6$^{th}$ (1994).

* cited by examiner

Primary Examiner—David Guzo
(74) Attorney, Agent, or Firm—Virginia C. Bennett

(57) ABSTRACT

The present invention provides a method for the propagation of lytic organisms which comprises the infection of the cells of a stable cell line within a hollow fibre bioreactor with a lytic organism, wherein after said infection, said organism multiplies within the cells and can be harvested, characterised in that the cell line can survive for at least ten days after said infection. The invention further provides a method as herein described wherein after harvest, the cell line is allowed to re-populate the bioreactor, and at least one subsequent harvest may be taken, with the cell line being able to repopulate the bioreactor after each harvest.

31 Claims, 6 Drawing Sheets

METHODS FOR THE PROPAGATION OF LYTIC ORGANISMS

Figure 1:
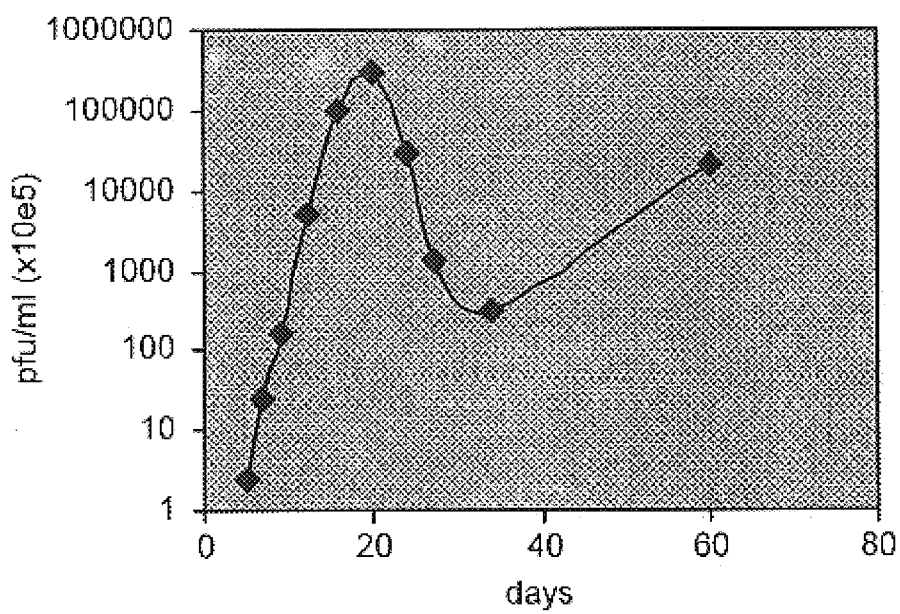

This application if filed pursuant to 35 U.S.C. §371 as a United States National Phase Application of International Application No. PCT/EP0005039 filed Jun. 2, 2000, which claims priority from Great Britain Application No. 9915413.0 filed Jul. 1, 1999.

The present invention relates to a method for the propagation of lytic organisms, and its use for the production of lytic organisms and proteins.

BACKGROUND

A number of different organisms can be grown in tissue culture for use in research studies or vaccine production. However, the titres obtained in tissue culture, although suitable for research purposes, are often too low to be commercially useful in the vaccine industry, so bulk preparations of vaccines (e.g. flu vaccine) are often cultured in chicken eggs. This system provides very high titres of virus but requires a large amount of processing and quality control of product before release. The process is very labour intensive and has problems with continuity of supply and reproducibility of product from batch to batch. Hence there is a need for large scale, reproducible, high titre production of organisms.

Another area that feels a critical need for large scale high titre reliable virus production is gene therapy. Recombinant adeno-associated virus vectors have recently been shown to be efficient, non-immunogenic and persistent vectors for gene therapy. However, current technologies are unable to produce the amounts of recombinant viruses needed for this field to move forward (Linden. R. M and Woo, S. L. C. Nature Medicine 5(1) 1999 pp 21–22.)

The culture of lytic organisms is particularly difficult as these quickly destroy the cell population they are grown in. The insect virus baculovirus is a lytic organism which can be used for the production of proteins. These viruses can be engineered for recombinant protein expression (Gruenwald, S. and Heitz, J. Baculovirus expression vector system: Procedures and methods manual. Pharmingen). They are generally grown in spinner culture, in which maximum infection and hence maximum protein production is reached after two days. A longer term culture of baculovirus would produce greater amounts of protein, and be extremely useful but, until now, has not been possible. Also, a continuous culture would provide a sustained supply of product, which until now has only been possible with batch processes requiring repeated cultures.

BRIEF DESCRIPTION OF THE INVENTION

The present invention provides a method for the propagation of lytic organisms which comprises the infection of the cells of a stable cell line within a hollow fibre bioreactor with a lytic organism, wherein after said infection, said organism multiplies within the cell line and can be harvested, characterised in that the cell line can survive for at least ten days after infection.

The invention further provides a method as described above, wherein the lytic organism contains nucleic acid encoding a protein of interest, and after said infection this protein is expressed by the cells and can be harvested.

Further provided is any of the methods as described herein which further comprises the step of harvesting of either the lytic organism or the expressed protein.

In another aspect of the invention is provided a method as described wherein after harvest, the cell line is allowed to re-populate the bioreactor, and at least one subsequent harvest may be taken, with the cell line being able to re-populate the bioreactor after each harvest. In this aspect the method is applicable both when the desired product is the lytic organism itself, or an expressed protein of interest.

Further provided is a method for studying the effects of molecules on a lytic organism which comprises the infection of the cells of a stable cell line within a hollow fibre bioreactor, wherein after said infection, varying amounts of said molecules may be added, and their effects on the lytic organism measured, characterised in that said cell line can survive for at least 10 days after infection.

FIGURES

FIG. 1: Adenovirus production in a hollow fibre bioreactor. This figure shows both the long term production before harvest (21 days) and the repopulation of the bioreactor, leading to further virus growth after harvest, up to 60 days.

Figure 2:
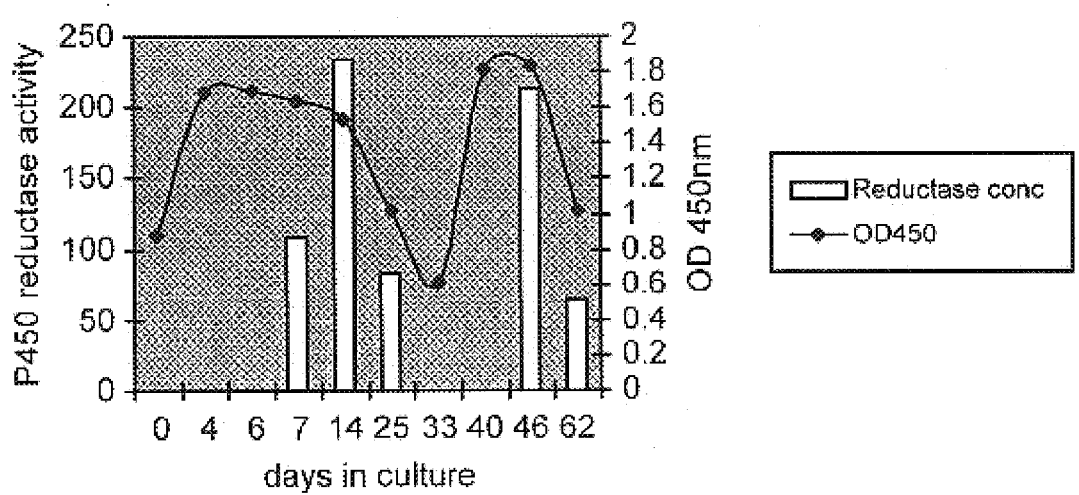

FIG. 2: Production of cytochrome p450 reductase after infection with baculovirus containing DNA encoding this protein. The OD450 (measured by Virus specific ELISA) is proportional to the viral titre, and the solid bars show the protein levels harvested in activity units. This graph indicates that long term and cyclical production of virus and expressed protein is possible.

Figure 3:
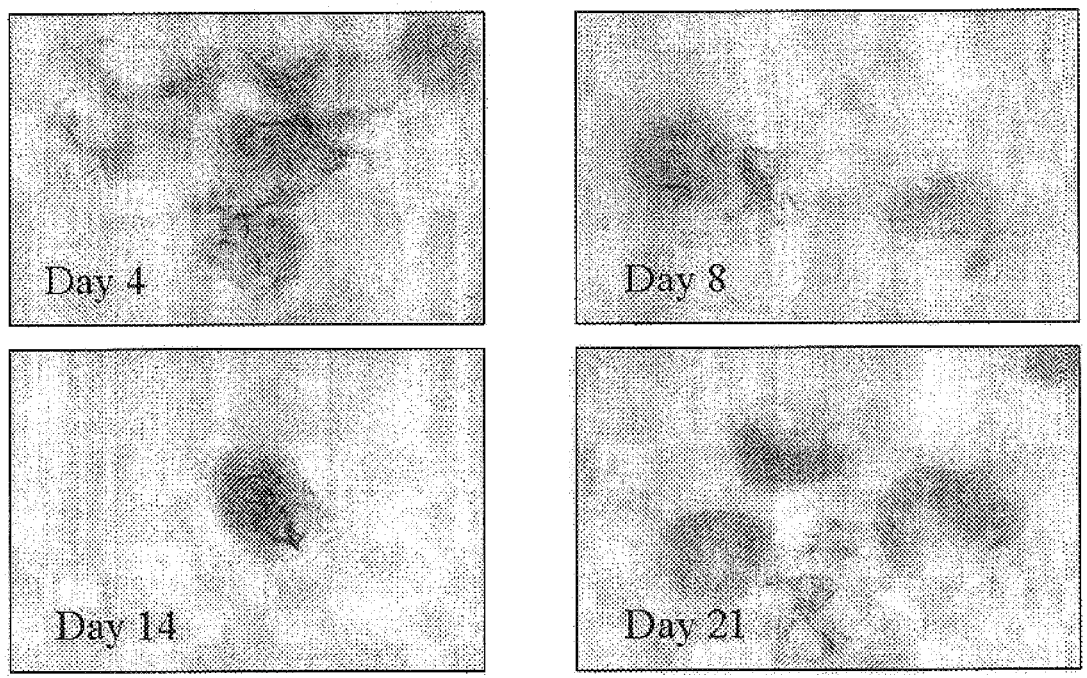

FIG. 3: Production of the mycobacterium BCG within THP-1 cells in a hollow fibre bioreactor. Samples were taken at 4, 8, 14 and 21 days after infection. The large circles are macrophage cells. This figure indicates long term survival of the cell line and production of BCG.

Figure 4:
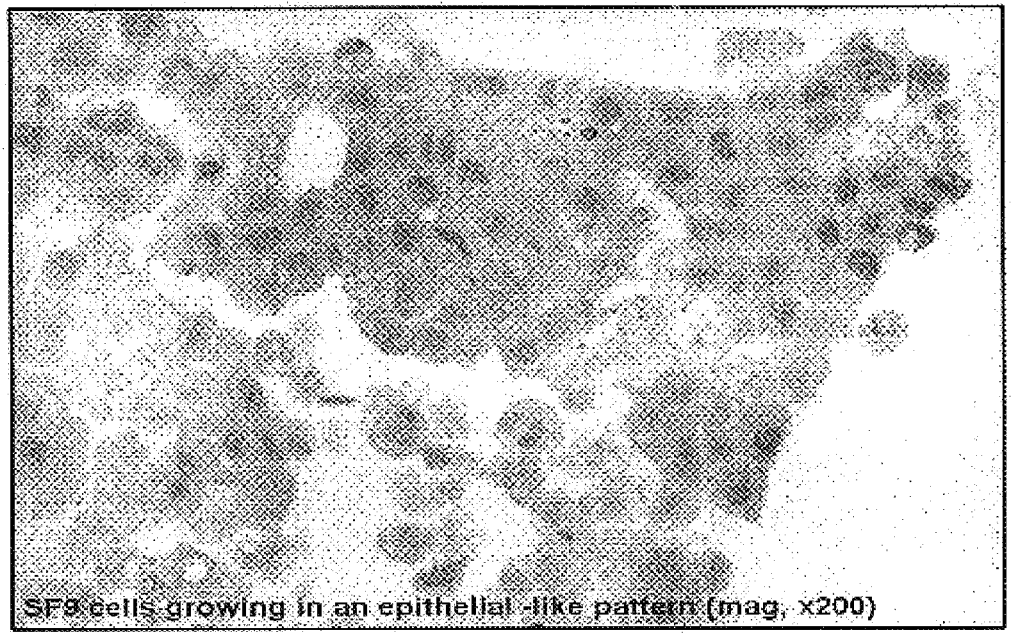
Figure 4:
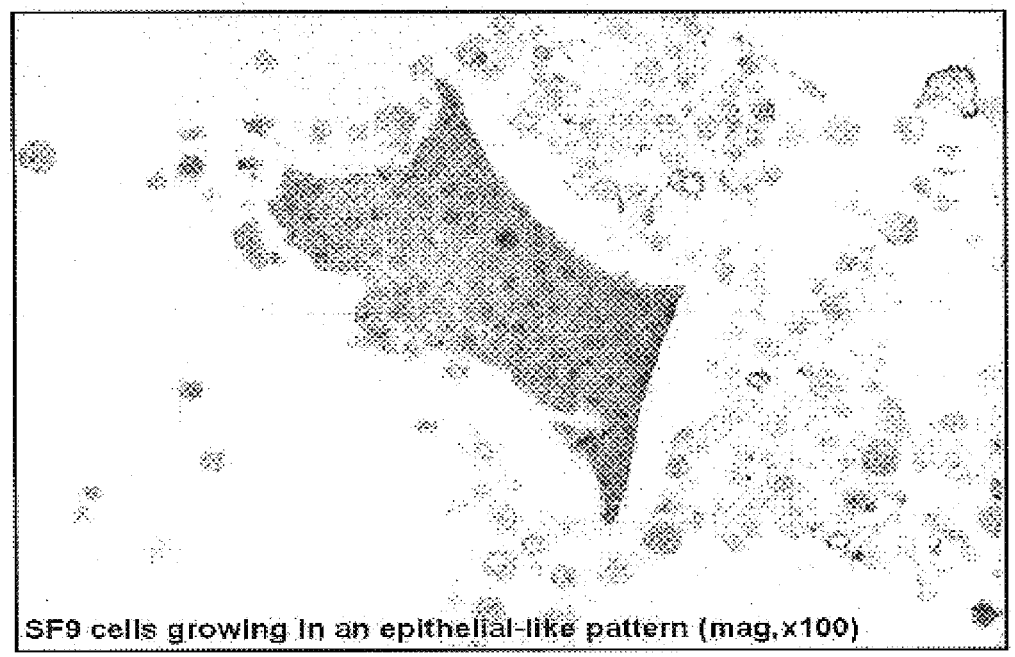

FIG. 4: This photograph shows the existence of "epithelial-like" structures within the cell.

Figure 5:
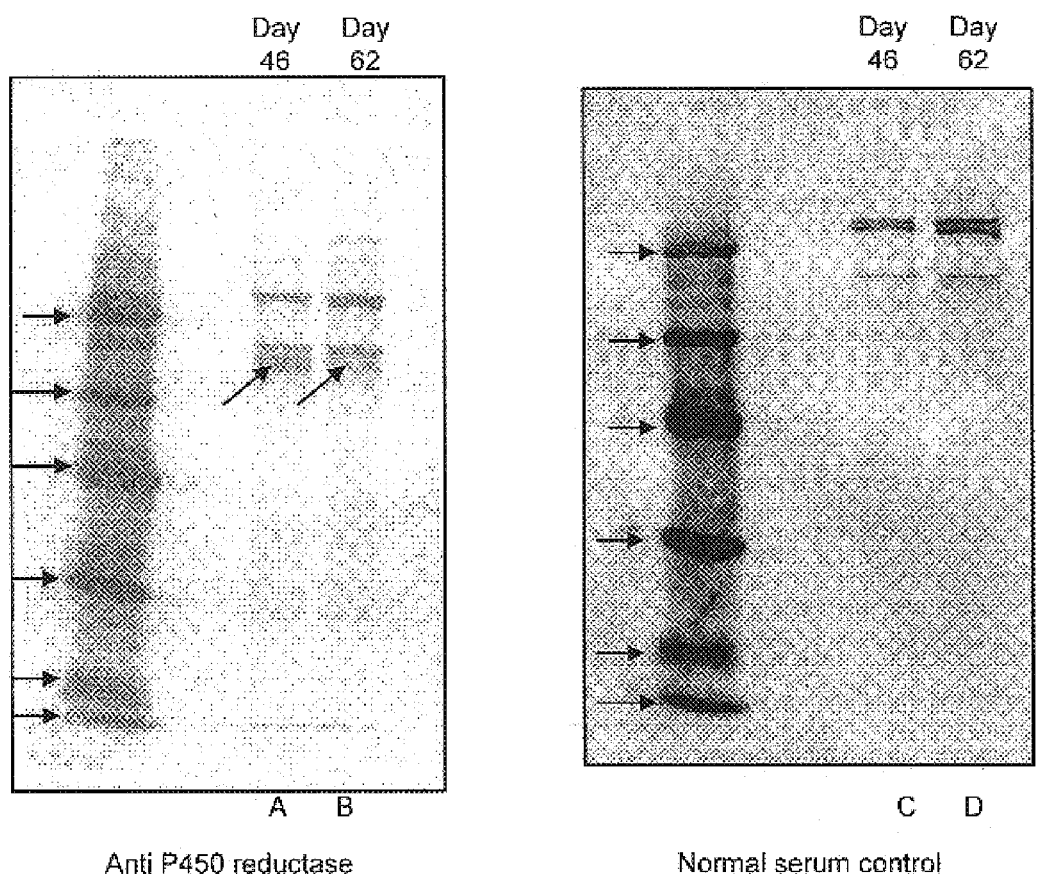

FIG. 5: Western blot analysis of p450 reductase expression in a hollow fibre bioreactor. This figure clearly show that p450 reductase is produced within the bioreactor up to day 62.

Figure 6:
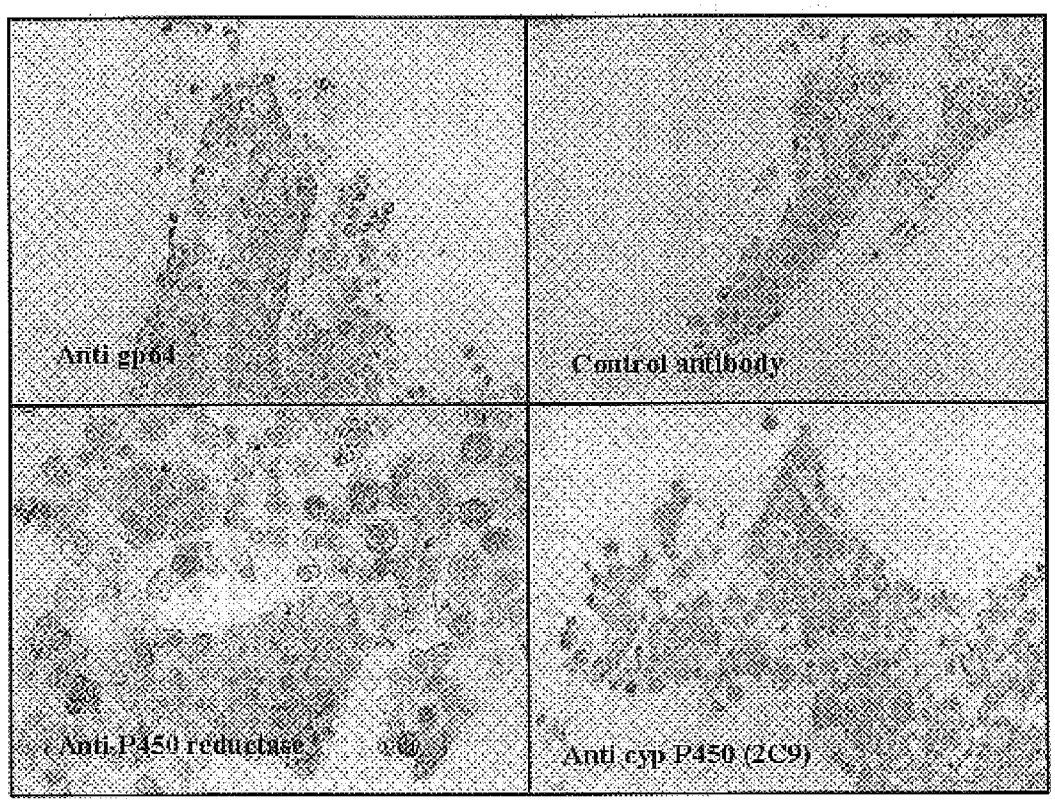

FIG. 6: Staining demonstrating extensive virus infection, P450 reductase and cytochrome P450 production within the bioreactor.

Figure 7:
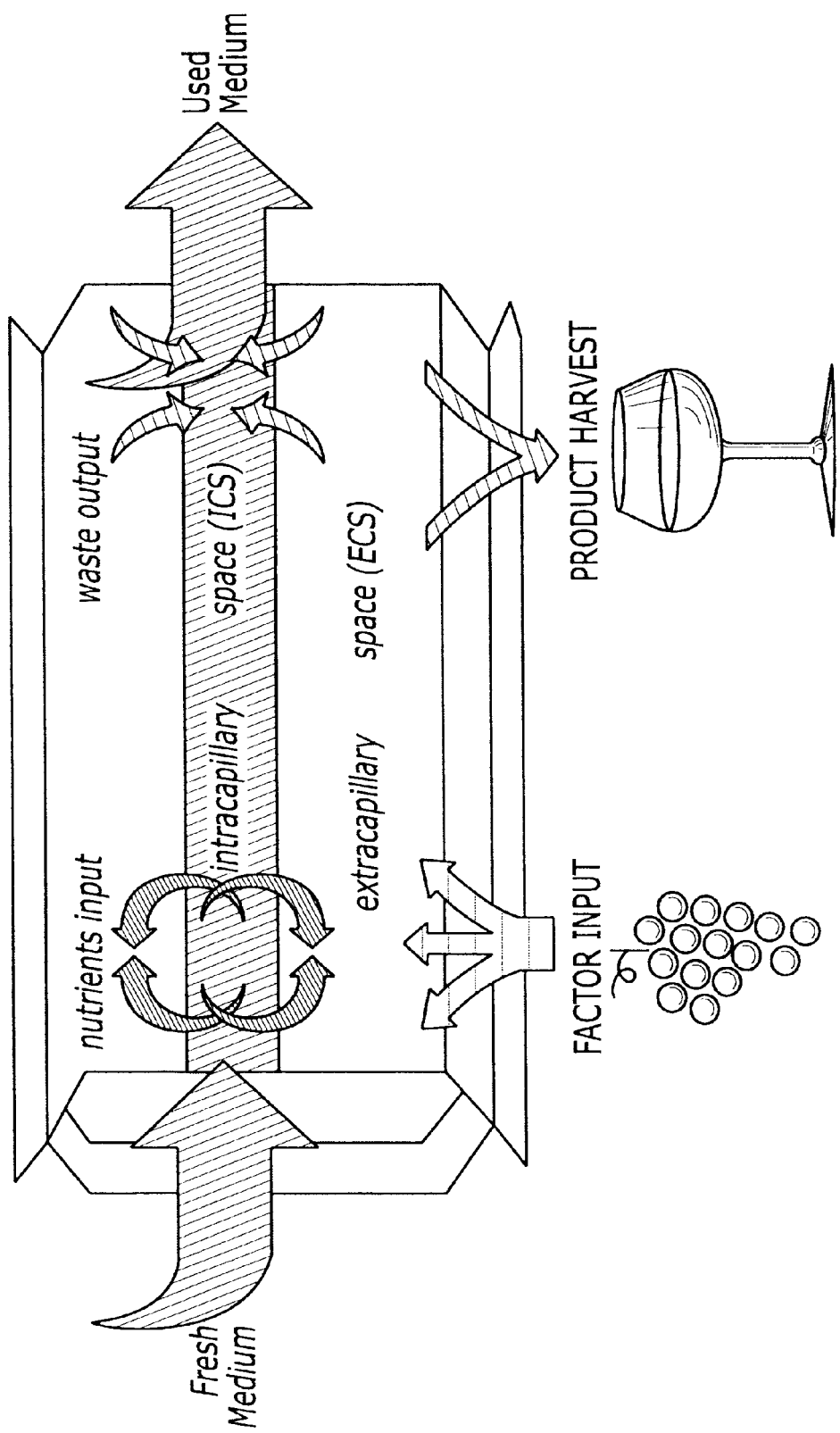

FIG. 7: A schematic of a hollow fibre bioreactor, demonstrating the nutrient and waste cycling, as well as factor input and product harvest.

DETAILED DESCRIPTION OF THE INVENTION

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

The present inventors have determined that use of a high cell density in the method of the invention allows the cell line to survive for longer periods following infection with a lytic organism than has previously been possible.

Hence in a first aspect of the invention, the cell line can survive for at least twelve days following infection, preferably at least 15 days, more preferably at least 20, 25 or 30 days. For the duration of the time that the cell line survives, the lytic organism is produced and can be harvested. Also, if the lytic organism contains nucleic acid encoding a protein of interest, this is expressed as long as the cell line survives, and harvests can be taken during this time.

Harvest of the lytic organism or the protein of interest in the method of the invention comprises removal of the organism or the protein from the bioreactor. This may be by any means, but preferably is by flushing of the medium from the bioreactor.

In a second aspect of the invention as described herein, the cell line is allowed to re-populate the bioreactor following harvest, and subsequent harvests may be taken. In this aspect, the method of the invention provides for continuous production of the lytic organism. Preferably at least two subsequent harvests may be taken, more preferably at least three, four, five, seven or nine subsequent harvests may be taken. Particularly preferred is when ten or more subsequent harvests for example 15, 20 or 25, may be taken. Repeated harvests may be taken for as long as the cell line survives, which in this aspect may be at least 15 days after infection, more preferably 20 days. Particularly preferred is when the cell line can survive for at least 25, 30, 40, 50, 60, 90, 120, 150 or 180 days after infection with the lytic organism. In fact, provided that the bioreactor does not undergo mechanical failure, or the cells within the bioreactor do not become infected by another organism, the cell line may survive indefinitely, for example several years. The time between harvests should be sufficient for the cells to repopulate the bioreactor to an appreciable extent, but may be as little as 1 day.

The repeated harvesting of product and repopulation of cells is thought to occur in the following way. Following addition of the lytic organism into the hollow fibre bioreactor containing the stable cell line, it seems that the lytic organism will infect some of the cells of that cell line, where it will multiply and cause subsequent lysis of these cells, releasing the lytic organism produced within that cell into the bioreactor. This will then go to infect more cells, multiply within them and cause their lysis. In this way the organism multiplies, and the cell line is gradually caused to lyse and die. However, due to the high cell density used in the method of the invention, it appears that the lytic organism will not undergo this cycle sufficiently frequently to infect all of the cells of the cell line before harvest. Due to the high density of cells present in the bioreactor, generally the cells form three dimensional arrays within the fibre matrix such that whilst the cells on the outside of the array may become infected, the cells on the inside of the array will not be infected before harvest. The structure of an array can clearly be seen in FIG. 4, and these arrays may be found throughout the bioreactor.

At harvest, most of the lytic organisms are removed, but some are allowed to remain inside the bioreactor. After harvest the bioreactor contains cells infected with the lytic organism which have not yet lysed and healthy, uninfected cells. At this point, if fresh medium is added to the bioreactor, the cells remaining within the bioreactor continue to divide and grow, and repopulate the bioreactor, providing a fresh population of cells for the cycle of infection and lysis to continue. In the situation where the lytic organism contains a nucleic acid encoding a protein of interest, the new population of cells will express this protein, which can be harvested. Thus in this aspect, the invention provides a method for cyclical continuous production of lytic organisms or a desired protein.

A Hollow fibre bioreactor as used in the method of the invention is a continuous perfusion system with a constant replenishment of nutrients and removal of wastes or products. Medium circulates through a micro-capillary bed of semipermeable fibres. The interior of the fibres is termed the Intracapillary space (ICS), and the exterior is termed the extracapillary space (ECS). Cells grow in the ECS, and adhere to the outside of the fibres. The fibres provide a large surface area for cell contact, in a relatively compact system.

Typically, small molecular weight cellular nutrients and metabolic waste products can pass between the ICS and the ECS whilst cells and lytic organism or expressed protein products are confined to the ECS. A "feed" or "factor addition" port is used to introduce the lytic organism, or to feed large molecular weight nutrients, into the ECS. A harvest port is used to remove the medium containing the harvest from the ECS. A schematic diagram of a bioreactor is shown in FIG. 7. One example of a typical hollow fibre bioreactor is BR1910 which is available from UNISYN® Technologies. The reactor employs multiple fibres consisting of semipermeable polymeric membranes. The material of which these membranes are made may vary. Preferably, however, the semipermeable polymeric membranes are made from cellulose acetate.

Infection comprises introducing the lytic organism into the ECS so that it may infect the cells of the stable cell line. Preferably, the lytic organism is introduced as a suspension, or more preferably as a seeder culture. A seeder culture comprises a small number of cells of the same cell line as that within the bioreactor. The cells of the seeder culture have been previously infected with the lytic organism. The infected seeder culture is introduced into the ECS, where the lytic organism causes the cells of the seeder culture to lyse. The lytic organism is hence released into the ECS, and proceeds to infect the cells within the bioreactor.

The term lytic organism as used throughout the specification and claims is intended to encompass any organism, whether in its natural state, or which has been modified genetically or in any other way, which is capable of infecting a cell and subsequently causing it to lyse. The lytic organism is destructive to the cells it infects. Multiplication of the organism within the cell leads to lysis and death of the cell and release of the organism into the surrounding medium. In the situation where the lytic organism contains nucleic acid encoding a protein of interest, this protein is expressed by the cell before lysis.

Typical lytic organisms encompass eukaryotes, prokaryotes, for example mycobacteria, and viruses, for example baculovirus; members of the Herpesviridae such as HSV1, HSV2, VZV, HCMV, HHV8; parvoviruses such as B19, AAV-2; members of the Togaviridae including alphaviruses such as equine encephalitis viruses & Sindbis and rubiviruses such as rubella; polyoma viruses such as SV40; arboviruses such as Getah arbovirus; diarrhoea viruses such as porcine epidemic diarrhoea virus; members of the Flaviviridae including flaviviruses such as yellow fever, dengue & encephalitis viruses, pestiviruses such as BVDV and unclassified viruses such as hepatitis C; members of the Bunyaviridae including phleboviruses, such as sandfly fever, nairoviruses, such as haemorrhagic fever viruses, hantaviruses, such as Hantaan and Sin Nombre, and bunyaviruses, such as bunyamwera; arenaviruses such as Lassa fever and lymphocytic choriomeningitis; astroviruses 1–5, caliciviruses such as Norwalk; members of the Reoviridae including the rotaviruses, orbiviruses and orthoreoviruses, such as bluetongue; members of the Picornaviridae including enteroviruses, such as poliovirus, ECHOvirus & coxsackievirus, rhinoviruses of all serotypes, hepatoviruses, such as hepatitis A, and aphthoviruses, such as FMDV; iridiviruses such as African seine fever virus; human and bovine papillomaviruses; filoviruses, such as Marburg and Ebola; poxviruses, such as smallpox, cowpox, variola and vaccinia; adenoviruses; orthomyxoviruses, such as influenzaviruses A,B & C and thogoto-like viruses; paramyxoviruses, such as all parainfluenzaviruses, mumps, measles, respiratory syncytial virus, Newcastle disease virus, animal distemper viruses & rinderpest. Also African swine fever virus, bovine leucosi and revirus. Preferably the lytic organism is a virus, more preferably it is an adenovirus or a baculovirus.

The present invention also extends to the infection with or production of modified lytic organisms. By modified is meant that the lytic organism has been altered in some way from the state in which it is found in nature. This may be, for example, by genetic manipulation, such as engineering the lytic organism to contain DNA encoding a protein of interest. Another example of genetic manipulation is where the lytic organism is engineered to contain or lack nucleic acid such that the resulting lytic organism is safer to use in therapy, such as a replication deficient, or less virulent organism. Lytic organisms can also be modified by other means, for example by attenuation.

The term stable cell line as referred to above is intended to encompass all cell lines that are capable of growing in the extra capillary space of the bioreactor to establish a population of $10^6$ cells per ml. At the point of infection with the lytic organism, the cells are preferably confluent. By confluent is meant that when examining the cells by eye, they have grown to cover the majority of the surface area. At the point of infection with the lytic organism, the cell density will preferably be $10^6$ cells per ml. More preferably the cell density will be $10^7$ cells per ml. Particularly preferred is when the cell density at the point of infection with the lytic organism is $10^8$ or $10^9$ cells per ml. It is thought to be due to the high cell density used in the method of the invention that the cell line can survive for so long after infection of the lytic organism. The cells are postulated to form a matrix, which prevents all the cells within the matrix becoming infected immediately, and hence allows the cell line to survive and proliferate for longer. An example of a matrix type structure within the bioreactor can be seen in FIG. 4.

Such cell lines include, for example, stable higher eukaryotic cell lines such as mammalian cell lines or insect cell lines, lower eukaryotic cell lines such as yeast cell lines or prokaryotic cell lines such as bacterial cell lines. The particular cell line chosen will vary depending on whether the desired product is a lytic organism, or whether the expression product of nucleic acid contained within the lytic organism is the desired product, and will depend also on the lytic organism used for infection. In the situation where the lytic organism contains nucleic acid encoding a protein of interest, and this protein is produced within the cell line, the cell line selected will preferably be one which allows for the correct post-translational modification of that protein to occur.

Particular examples of cell lines which can be used are vero cells which are susceptible to many typical lytic organisms as described above, for example adenovirus 12, African swine fever virus, arbovirus, bluetongue virus, echovirus, Getah arbovirus, herpes simplex virus, influenza virus, orbivirus, orthomyxovirus, paramyxovirus, poliovirus 3, porcine epidemic diarrhea virus, rheovirus and rubella; Hep-2C cells which are susceptible to for example arbovirus and measles virus; PerC6 cells which are susceptible to, for example adenovirus; SF9 or Tni cells which are susceptible to, for example baculovirus, and human macrophage cell lines such as THP-1 which is susceptible to, for example mycobacteria such as tuberculosis or BCG.

It will be understood by a person skilled in the art that the conditions within the bioreactor may vary depending on which cell line is used, which lytic organism is used for infection, and whether the desired product is a lytic organism, or the expression product of nucleic acid contained within a lytic organism. Particularly, the medium used will vary depending on the cell line. For example when using a mammalian cell line such as Vero cells, THP-1 cells or PerC6 cells, the medium is preferably DMEM, RPMI, Ham's F12, or similar medium or a custom derived medium specific for each cell line. When using an insect cell line such as Tni or SF-9, the medium is preferably SF900II, TC100 or similar insect cell medium. Supplements, for example antibiotics, feotal calf serum (FCS), glutamax™, δ-Aminolaevulinic Acid, ferric citrate, nicotinic acid, riboflavin and hemin chloride may be added when necessary, for example when producing a specific protein.

The nucleic acid referred to in the specification and the claims as being contained within the lytic organism may be in the form of RNA or DNA, for example cDNA, genomic DNA, or synthetic DNA. The nucleic acid can be, for example, a whole gene, the coding region of a gene, a desired fragment of a gene or a wholly synthetic nucleic acid, depending on the protein required.

The term protein as used throughout the specification and the claims includes within its meaning full length proteins, truncated proteins, chimaeric proteins, fragments of proteins, for example an antigenic portion or a ligand binding site, and wholly synthetic polypeptides of any desired length. Also included within the definition of protein are variants thereof, meaning that the protein has been modified by the deletion, modification or addition of single amino acids or groups of amino acids within the protein sequence.

Examples of proteins which can be produced include, but are not limited to, recptors, cytokines, growth factors, adhesion molecules for example ICAM, and enzymes, for example cytochrome p450 reductase or tyrosine kinase, and fragments or variants thereof.

The nucleic acid which may be contained within the lytic organism may encode one, two, three, four or more proteins of interest. There are several ways in which the lytic organism can be engineered such that more than one protein is expressed. For example, two or more genes may be contained on the same plasmid. They may be under the control of one promoter, each gene separated by, for example, an internal ribosomal entry site (IRES). Alternatively, they may be under the control of separate promoters. In this situation, the only limit to the number of proteins which may be contained within a vector or plasmid is the cloning capacity of the vector. Theoretically, large numbers of proteins may be expressed. Preferably, however, three or fewer proteins are expressed, more preferably only one or two proteins are expressed. Particularly preferred is the method of the invention wherein the lytic organism is baculovinis, and two genes encoding proteins of interest are present, one under the control of the P10 promoter, and one under the control of the polyhedrin promoter.

In another embodiment, the genes may be contained on a multicistronic plasmid, or indeed may be contained on different plasmids, each plasmid containing one or more genes encoding proteins of interest. In a further embodiment, one lytic organism may be engineered to contain nucleic acid encoding a protein of interest, and another lytic organism may be engineered to contain nucleic acid encoding another protein of interest, and both organisms may be included in the seeder culture. This method may extend to three, four or more lytic organisms, each containing nucleic acid encoding one or more proteins of interest.

Production of more than one protein of interest is preferred, for example, where an expressed protein requires the presence of another protein for activation, for example cytochrome p450 and cytochrome p450 reductase or proteins that require dephosphorylation and their kinases. Production of more than one protein of interest in the method of the invention is further preferred as a way of producing large amounts in one system of the components of assay systems, for example proteins for yeast two hybrid screens; proteins for yeast three hybrid screens; receptors and ligands for ligand binding assays. In another example, production of more than one protein in the method of the invention may be used to co-produce proteins of interest and marker proteins such as beta glactosidase or green fluorescent protein.

In another aspect of the invention is provided a method for studying the effects of molecules on a lytic organism which comprises infection of the cells of a stable cell line within a hollow fibre bioreactor wherein after said infection, varying amounts of said molecules may be added, and their effects on the lytic organism measured, characterised in that said cell line can survive for at least ten days after infection. Thus is provided, for example, a means of testing the effect of drugs on the infectivity or life cycle of an organism, or a means of testing the pharmacokinetics or pharmacodynamics of drugs during an infection caused by a lytic organism. As the present invention provides longer term survival of the cell line after infection than existing systems, drug interactions and effects can be studied over a longer time period, opening the possibility of using the system for looking at the effect of molecules on chronic infections for example Herpes Simplex Virus, Papilloma virus, or mycobacterial infections. The method may also provide an in-vitro model for diseases other than infectious diseases, for example respiratory or cardiovascular disease.

EXAMPLES

Example 1
Cyclical Production of Mammalian Virus

For adenovirus specifically, the cells used are PerC6 cells (introgene). However, this method is applicable to all mammalian cell lines and mammalian viruses described in the specification.

Cells were grown in 6×175 sq.cm. flasks in DMEM (Life Technologies) supplemented with 2 mM glutamax™ (Life Technologies), 5% FCS (Life Technologies). The cells were scraped off or aspirated off at confluence and transferred to the extracapillary space (ECS) of a BR1910 (Unisyn Technologies) hollow fibre bioreactor (19 sq.ft surface area, 10 kD molecular weight cut off, membrane material cellulose acetate). Routinely around 10e8 cells are inoculated into the ECS of each BR1910. The intracapillary space (ICS) was constantly perfused with DMEM {Life Technologies} supplemented with 2 mM glutamax™ (Life Technologies) at a recirculation rate of 100–500 ml/min. The re-circulation rate is low at the time of inoculation and the rate increases with time in culture as the cell density within the bioreactor increases. The recirculating medium was held in a reservoir containing 1.0 liter, with a continuous medium change via a feed and harvest skimmer system of 0.8 liters/day to 2.0 liter/day. The feed rate is set low at inoculation and increases with cell density over time. The medium was oxygenated by an OXY10 (Unisyn Technologies) oxygenation cartridge (10 sq.ft. surface area, pore size 0.2 um, membrane material microporous polyethylene fibre) perfused with 95% air/5% CO2 at a pressure of 2 psi. Cells were then grown until the bioreactor was deemed to be confluent by eye (usually between 20 and 80 days). The cell mass in the ECS received regular feeding by exchanging 50 ml of the spent ECS medium with 50 ml fresh medium consisting of DMEM(Life Technologies)/5%FCS(Life Technologies)/2 mMglutamax (Life Technologies) at intervals not less than weekly. Fresh medium is introduced and spent medium removed via the feed and harvest ports in the bioreactor. Virus was inoculated into the ECS via one of the feed and harvest ports, and the infection allowed to continue until a suitable harvest point. In the first instance, samples were taken to monitor progress of the infection, and harvests were taken subsequently at 7–10 day intervals. The ECS was extensively harvested by flushing with 2×50 ml aliquots of culture medium and by passing medium across the membrane—ie from ICS to ECS, and the product stored for subsequent analysis. The cell mass in the ECS was then allowed to regenerate by feeding with DMEM (Life Technologies) supplemented with 2 mM glutamax™ (Life Technologies), 5% FCS (Life Technologies), and virus titre was monitored to determine the "recovery" phase. See FIG. 1 for results.

Example 2
Production of a Protein of Interest from a Baculovirus Containing DNA Encoding that Protein The cells were SF9 cells, at a concentration of around $10^6$ cells/ml. The cells were maintained using standard methodologies, with a passage frequency of 3–4 days. The medium used is a specialist insect cell culture medium, SF900 II (supplemented), obtained from Life Technologies (Cat. No.041-94322). This is also made up to contain Ultra Low IgG Foetal Bovine Serum (U.S.) at a concentration of 10%, that was also obtained from Life Technologies (Cal.No.10118-164).

In order to inoculate the bioreactor, it is necessary to produce around 10e8 cells. Thus 4×225 $cm^2$ tissue culture flasks are inoculated to produce these cells. Inoculation of the cells is carried out via the factor addition port of the bioreactor, into the ECS. Excess medium is removed via the harvest port. Once the cells are inoculated, the feed and harvest ports are closed, and the re-circulation and feed/waste pumps are switched on.

The cells are left for 7–21 days in order to adapt to their new situation, before infection with virus occurs. This period can be longer if required, as the cells can be maintained in the bioreactor indefinitely. During this period air should be run through the oxygenator to saturate the medium with oxygen. The pumps should be running at between 0.8 and 2 liters/day for the feed and waste skimmer pump (increasing with cell density), and the re-circulation pump at around 100–500 ml/min(also increasing with cell density) .The temperature should be a constant 27° C. The infection with virus is carried out at a multiplicity of infection (MOI) estimated to be 1.0. Thus the volume of virus suspension that should be added will depend on the concentration of virus (in PFU/ml) and the number of cells present in the bioreactor. Addition of the virus is done through the factor addition port, along with SF900 and the required volume of any necessary supplements (see example 4). Some of the medium forced out of the harvest port is retained to give a time 0 sample. The bioreactor is then sampled at day 2, 4 and 6, and at subsequent weekly intervals to monitor the infection. Initially samples should be of 50 ml, taken while adding fresh medium, FCS and other supplements. Larger harvests are taken as detailed in example 1. These large samples are then carried out on a weekly basis to monitor long term virus and protein production. As in example 1, this system can be operated in a cyclical manner by allowing the cell mass to regenerate by feeding with fresh medium, and any necessary supplements.

Example 3
Production of Cytochrome p450 and cytochrome P450 Reductase from Baculovirus.

This is essentially as described in example 2. However, due to the abnormally high levels of P450 and P450 reductase expression that should occur in the system if these proteins are being produced, the cells will require higher than normal levels of certain nutrients, in order to maintain their intracellular reservoirs. To this end the cells are supplied with certain supplements:

δ-Aminolaevulinic Acid (δALA) at 0.1 mM,
Ferric Citrate at 0.1 mM,
Nicotinic Acid at 0.05 $\mu$M,
Riboflavin at 0.01 $\mu$M,
Hemin Chloride at 2 mg/l solution.

All these supplements were obtained from Sigma Biosciences, and made up as stock solutions using SF900 medium as before. The exceptions are ferric citrate, which should be dissolved in boiling water, and hemin chloride, which should be dissolved in 0.1M sodium hydroxide after which an equal volume of water should be added. These supplements are used in the concentrations indicated, and should be added to both the bioreactor ECS and the feed bottle/bag in order to maintain the required concentration throughout the system. Note that these supplements are only required once the cells have been infected with the baculovirus and if the baculovirus insert contains the P450 and reductase genes. Inserts not producing P450 will not require the supplements.

See FIG. 2 for results. This graph indicates that long term production is possible with this method, with significant amounts of protein being harvested at 14 days after infection, a much longer term than has been possible before. It can also be clearly seen from the graph that cyclical production of the protein is possible, with a subsequent increase both in virus titre and protein production after the first harvest.

Expression of P450 reductase was confirmed by western blot analysis of samples taken from the bioreactor. Western blotting was carried out using a method which is a modification of the Laemmli technique (Laemmli U.K. Nature 227 pp 680–685). FIG. 5 shows the results. Samples were taken at day 46 (lanes a and c) and day 62 (lanes b and d). Samples were run on 10% polyacrylamide gels under reducing conditions and blotted onto nitrocellulose membranes. The blots were probed with sheep anti-P450 reductase (a and b) or control sheep serum (c and d). The data shown in FIG. 5 demonstrates the staining of a band of protein at Mr 78kD which is absent in the control serum tracks. P450 reductase has a MW of 78kD. These pictures clearly show that p450 reductase is produced up until day 62.

Confirmation of viral infection and production of both proteins can be seen in FIG. 6. Fixation was carried out as described in example 5 below. However, biotinylated anti-GP64 antibody was used to identify those cells expressing baculoviral GP64 protein. Sheep anti P450 and sheep anti P450 reductase was used to visulaise the presence of these proteins. A streptavidin-conjugated peroxidase was then used to stain antigen positive cells. FIG. 6 clearly shows production of P450 and P450 reductase, although p450 stains more weakly, as it is less stable than the P450 reductase. This figure also indicates that extensive viral infection is confined to the outer face of the cell array.

Example 4
Production of BCG

THP-1 cells were grown in 6×175 sq.cm. flasks in DMEM (Life Technologies) supplemented with 2 mM glutamax™ (Life Technologies), 5% FCS (Life Technologies). The cells were scraped off or aspirated off at confluence and transferred to the extracapillary space (ECS) of a BR1910 (Unisyn Technologies) hollow fibre bioreactor (19 sq.ft surface area, 10 kD molecular weight cut off, membrane material cellulose acetate). Routinely around $10e^8$ cells are inoculated into the ECS of each BR1910. The intracapillary space (ICS) was constantly perfused with DMEM {Life Technologies}supplemented with 2 mM glutamax™ (Life Technologies), at a recirculation rate of 100–500 ml/min. The re-circulation rate is low at the time of inoculation and the rate increases with time in culture as the cell density within the bioreactor increases. The recirculating medium was held in a reservoir containing 1.0 liter, with a continuous medium change via a feed and harvest skimmer system of 0.8 liters/day to 2.0 liter /day. The feed rate is set low at inoculation and increases with cell density over time. The medium was oxygenated by an OXY10 (Unisyn Technologies) oxygenation cartridge (10 sq.ft. surface area, pore size 0.2 um, membrane material microporous polyethylene fibre) perfused with 95% air/5% CO2 at a pressure of 2 psi. Cells were then grown for three weeks. The cell mass in the ECS received regular feeding by exchanging 50 ml of the spent ECS medium with 50 ml fresh medium consisting of DMEM(Life Technologies)/5%FCS(Life Technologies)/2 mMglutamax (Life Technologies) at intervals not less than weekly. Fresh medium is introduced and spent medium removed via the feed and harvest ports in the bioreactor.

The cell mass at confluence was treated with phorbol myristic acid (PMA) at 5 ng/ml to induce differentiation. 24 hours after differentiation, $10e^8$ cfu of BCG were added to the bioreactor, and infection monitored by sampling at time intervals over 30 days. Final harvests were by flushing the ECS with medium, flushing medium across the membrane, flushing out the ECS in 2% SDS, and finally 5 mM arabinose.

Samples were retained for analysis. See FIG. 3 for results of infection. These results demonstrate long term survival of the cell line and production of BCG.

Example 5
Bioreactor Fixation to Examine the Internal Structure of the Cell Mass The ECS was filled with neutral buffered formalin (2% formaldehyde in PBS) to fix the cells. In order to provide some support to maintain the structure inside the bioreactor, molten agarose (2% agarose in PBS) was pumped into the ICS and allowed to set. To support the ECS 2% formalin containing 2% agarose was then forced into the ECS using the feed and harvest ports. This was also allowed to set. The entire bioreactor cartridge was then cut away from the recirculation loop inside a biological safety cabinet. Using a hacksaw the top and bottom of the cartiridge were removed to leave a cylinder which contained the fixed cells. It was then possible to carefully push the fixed contents of the cartridge from one end of the cylinder. The cellular architecture within the bioreactor is maintained if this is done carefully. As the contents were pushed out, a razor blade was used to slice off aliquots of the fixed material around 4–5 cm thick, which was then dropped into neutral buffered formalin for starage. Once the bioreactor contents were fixed they were embedded in paraffin and cut to a thickness of around 5 um using a microtome. They were then mounted on slides ready for staining.

The photograph shown in FIG. 4 is a result of staining with haematoxylin and Eosin according to standard protocols. The picture indicates the presence of matrix-like cell structures.

The application of which this description and claims forms part may be used as a basis for priority in respect of any subsequent application. The claims of such subsequent application may be directed to any feature or combination of features described herein. They may take the form of product, composition, process or use claims and may include, by way of example and without limitation, one or more of the following claims:

What is claimed is:

1. A method for the propagation of lytic organisms, comprising:
   a) providing a hollow fiber bioreactor containing multiple hollow fibers, and having a stable cell line growing in the extracapillary space (ECS) of said hollow fiber bioreactor at a cell density of $10^4$ cells per milliliter or greater;
   b) introducing a lytic organism into said ECS, said lytic organism of a type capable of infecting said stable cell line; and
   c) allowing said lytic organism to infect, and multiply within, the cells of the stable cell line.

2. A method according to claim 1 where said stable cell line is selected from mammalian cell lines, insect cell lines, yeast cell lines and bacterial cell lines.

3. A method according to claim 1, further comprising harvesting said lytic organism from the hollow fiber bioreactor.

4. A method according to claim 1 where said lytic organism is a virus.

5. A method according to claim 1 where said stable cell line survives in the hollow fiber bioreactor for at least 10 days after infection.

6. A method according to claim 3 further comprising, after said harvest, repopulating said hollow fiber bioreactor with said stable cell line remaining after the harvest.

7. A method for the propagation of lytic organisms, comprising:
   (a) providing a hollow fiber bioreactor containing multiple hollow fibers, and having a stable cell line growing in the extracapillary space (ECS) of said hollow fiber bioreactor;
   (b) introducing a lytic organism into said ECS, said lytic organism of a type capable of infecting said stable cell line, and where said lytic organism contains nucleic acid encoding a protein of interest that is expressed in the stable cell line following infection by the lytic organism;
   (c) allowing said lytic organism to infect, and multiply within, the cells of the stable cell line.

8. A method according to claim 7 further comprising the step of harvesting said protein of interest from the hollow fiber bioreactor.

9. A method according to claim 7 where said stable cell line has established a cell density within the ECS of $10^6$ cells per milliliter or greater prior to introduction of the lytic organism.

10. A method according to claim 7 where said stable cell line is selected from mammalian cell lines, insect cell lines, yeast cell lines and bacterial cell lines.

11. A method according to claim 7, further comprising harvesting said lytic organism from the hollow fiber bioreactor.

12. A method according to claim 7 where said stable cell line survives in the hollow fiber bioreactor for at least 10 days after infection.

13. A method according to claim 7 where said lytic organism is a virus.

14. A method according to claim 7 where said lytic organism is a baculovirus.

15. A method according to claim 7 where said lytic organism is an adenovirus.

16. A method for the propagation of lytic organisms, comprising:
   (a) providing a hollow fiber bioreactor containing multiple hollow fibers, and having a stable cell line growing in the extracapillary space (ECS) of said hollow fiber bioreactor;
   (b) introducing a lytic organism into said ECS, said lytic organism of a type capable of infecting said stable cell line, and where;
   (c) allowing said lytic organism to infect, and multiply within, the cells of the stable cell line, and where stable cell line survives in the hollow fiber bioreactor for at least 10 days after infection.

17. A method according to claim 16 where said stable cell line survives in the hollow fiber bioreactor for at least 15 days after infection.

18. A method according to claim 16 where said stable cell line survives in the hollow fiber bioreactor for at least 20 days after infection.

19. A method according to claim 16 where said stable cell line is selected from mammalian cell lines, insect cell lines, yeast cell lines and bacterial cell lines.

20. A method according to claim 16, further comprising harvesting said lytic organism from the hollow fiber bioreactor.

21. A method according to claim 16 where said lytic organism is a virus.

22. A method according to claim 16 where said lytic organism is a baculovirus.

23. A method according to claim 16 where said lytic organism is an adenovirus.

24. A method according to claim 16 where said stable cell line has established a cell density within the ECS of $10^6$ cells per milliliter or greater prior to introduction of the lytic organism.

25. A method according to claim 4 where said virus is a baculovirus.

26. A method according to claim 4 where said virus is an adenovirus.

27. A hollow fiber bioreactor comprising: multiple hollow fibers arranged to form an extracapillary space (ECS); a stable cell line growing in said ECS at a density of at least $10^4$ cells per milliliter; and a lytic organism of a type capable of infecting and lysing cells of said stable cell line.

28. A hollow fiber bioreactor according to claim 27, where said stable cell line is selected from mammalian cell lines, insect cell lines, yeast cell lines and bacterial cell lines.

29. A hollow fiber bioreactor according to claim 27 where said lytic organism is a virus.

30. A hollow fiber bioreactor according to claim 27 where said lytic organism is a baculovirus.

31. A hollow fiber bioreactor according to claim 27 where said lytic organism is an adenovirus.

* * * * *